United States Patent
Augustine

(10) Patent No.: US 8,469,690 B2
(45) Date of Patent: Jun. 25, 2013

(54) APPARATUS FOR SEVERING AND COLLECTING IV TUBING TIPS

(75) Inventor: Joseph G. Augustine, Phoenix, AZ (US)

(73) Assignee: Engineering & Research Associates, Inc., Tucson, AZ (US)

( * ) Notice: Subject to any disclaimer, the term of this patent is extended or adjusted under 35 U.S.C. 154(b) by 219 days.

(21) Appl. No.: 12/939,451

(22) Filed: Nov. 4, 2010

(65) Prior Publication Data

US 2011/0045116 A1    Feb. 24, 2011

Related U.S. Application Data

(60) Division of application No. 12/502,620, filed on Jul. 14, 2009, now Pat. No. 8,029,712, and a continuation-in-part of application No. 12/102,675, filed on Apr. 14, 2008, now Pat. No. 7,744,805, which is a division of application No. 11/555,172, filed on Oct. 31, 2006, now Pat. No. 7,438,548.

(60) Provisional application No. 61/081,969, filed on Jul. 18, 2008, provisional application No. 60/762,204, filed on Jan. 25, 2006, provisional application No. 60/732,118, filed on Oct. 31, 2005.

(51) Int. Cl.
*B29C 57/00* (2006.01)

(52) U.S. Cl.
USPC ........... 425/215; 425/292; 425/298; 425/392; 425/393

(58) Field of Classification Search
USPC ................. 425/169, 215, 292, 298, 392, 393
See application file for complete search history.

(56) References Cited

U.S. PATENT DOCUMENTS

| | | | |
|---|---|---|---|
| 3,888,647 A | 6/1975 | Breeden et al. | |
| 4,013,860 A | 3/1977 | Hosterman et al. | |
| 4,186,292 A | 1/1980 | Acker | |
| 4,390,832 A | 6/1983 | Taylor | |
| 4,490,598 A | 12/1984 | Minney et al. | |
| 4,529,859 A | 7/1985 | Minney et al. | |
| 4,661,300 A * | 4/1987 | Daugherty | 264/40.6 |
| 4,878,826 A | 11/1989 | Wendt | |
| 4,914,267 A | 4/1990 | Derbyshire | |
| 5,088,911 A | 2/1992 | Kumazaki | |
| 5,160,396 A | 11/1992 | Jensen et al. | |
| 5,360,330 A | 11/1994 | Jensen et al. | |
| 5,716,572 A * | 2/1998 | Lesiczka et al. | 264/161 |
| 5,736,085 A * | 4/1998 | Brown et al. | 264/161 |

* cited by examiner

*Primary Examiner* — Yogendra Gupta
*Assistant Examiner* — Joseph Leyson
(74) *Attorney, Agent, or Firm* — The von Hellens Law Firm, Ltd.

(57) ABSTRACT

Mandrel supported IV tubing is inserted within a mold of a mold assembly to heat the IV tubing and form a tapered end of the tubing. The tip of the tubing extending beyond the tapered end of the tubing is severed by the mandrel bearing against the mold to lodge the tip in an outlet of the mold. Cooling air is introduced to the mold assembly to cool the mold and to create a flow of turbulent air about the outlet of the mold to extract the severed tips. The turbulent air is exhausted through a channel, pipe and fitting into a collection chamber and causes translation of the severed tip to and into the collection chamber. Sensors may be incorporated to sense the translation of the severed tips.

15 Claims, 8 Drawing Sheets

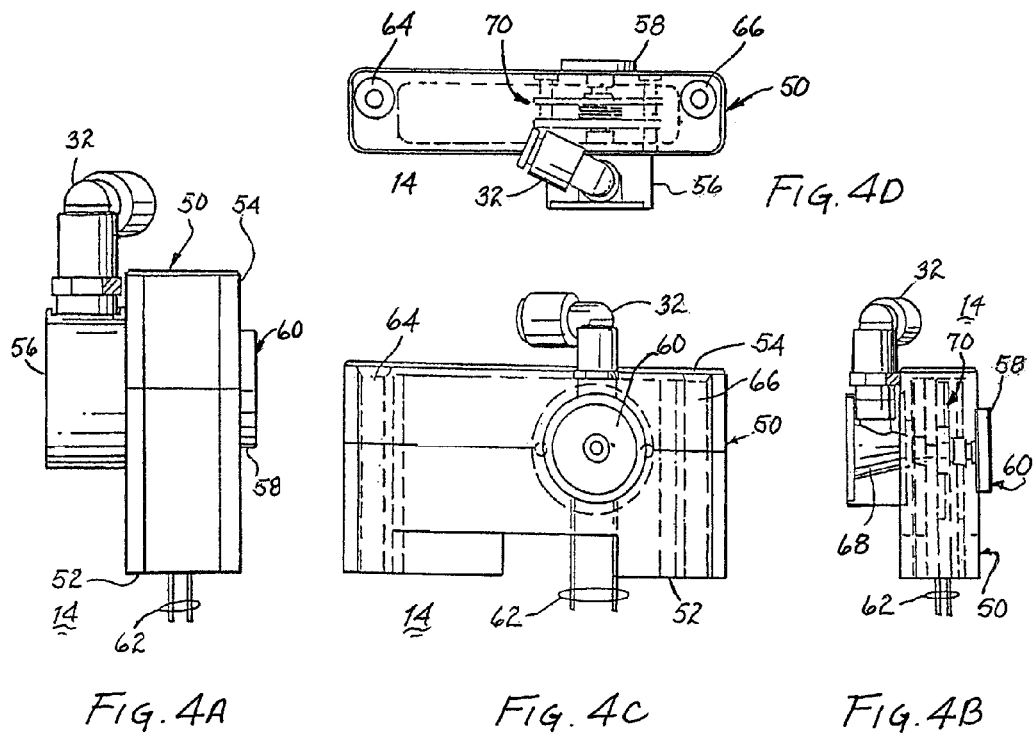
FIG. 4D
FIG. 4A   FIG. 4C   FIG. 4B
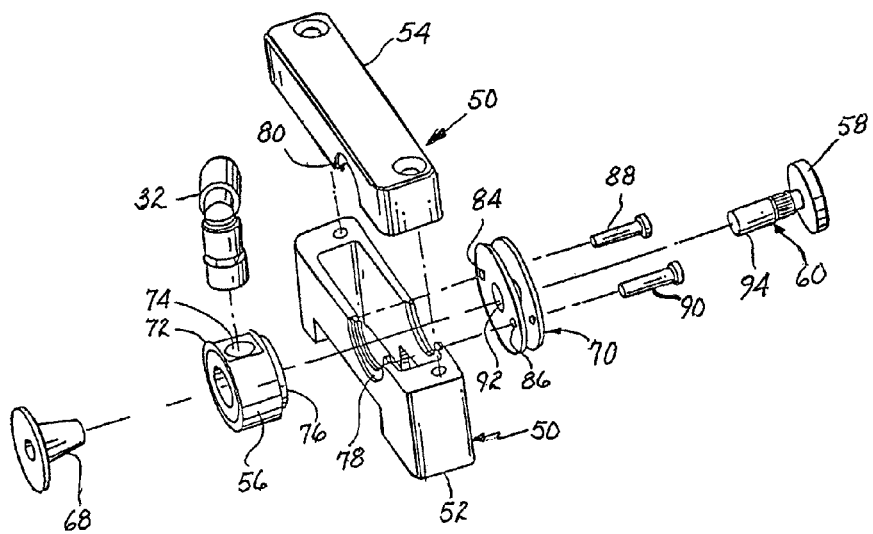
FIG. 5

APPARATUS FOR SEVERING AND COLLECTING IV TUBING TIPS

CROSS REFERENCE TO RELATED APPLICATIONS

The present application is a divisional of an application entitled "METHOD AND APPARATUS FOR COLLECTING IV TUBING TIPS" filed Jul. 14, 2009 and assigned Ser. No. 12/502,620 which is related to and claims priority to a provisional application entitled "METHOD FOR RAPIDLY HEATING AND COOLING A MOLD" filed Jul. 18, 2008, and assigned Ser. No. 61/081,969 and is a continuation-in-part application of an application entitled "METHOD FOR RAPIDLY HEATING AND COOLING A MOLD" filed Apr. 14, 2008 and assigned Ser. No. 12/102,675 which is a divisional of an application entitled "APPARATUS FOR RAPIDLY HEATING AND COOLING A MOLD", filed Oct. 31, 2006 and assigned Ser. No. 11/555,172, which in turn is related to and claims priority from a provisional patent application entitled "ASSEMBLY FOR RAPIDLY HEATING AND COOLING A CATHETER MOLD" filed Jan. 25, 2006 and assigned Ser. No. 60/762,204 and a further provisional application entitled "RAPID HEATING AND COOLING MOLD" filed Oct. 31, 2005 and assigned Ser. No. 60/732,118.

BACKGROUND OF THE INVENTION

1. Field of the Invention

The present invention relates to apparatus for rapidly heating and cooling a mold for forming, molding or welding thermoplastic tubing and, more particularly, to apparatus for severing, and collecting the tips of the tubing after a tip cutting process.

2. Description of Related Prior Art

Molds used for forming, molding and welding plastic tubing have employed a resistive element associated with the mold and the tubing to be formed is disposed within the mold. Inductive heating of the mold has also been employed. Such heating has been at a fixed location on the mold without the capability of varying the location of application of heat.

Molds used for forming, molding and welding tubing have been cooled primarily through the use of massive heat sinks. The rate of cooling of the mold to permit withdrawal of the formed tubing is a function of the ambient temperature and the massiveness of the heat sinks. Furthermore, some benefit has been achieved through dissipation of heat by radiation from finned heat sinks. Nevertheless, a significant time period is required to achieve the requisite cooling of the mold to permit withdrawal of the formed tubing. Such time constraints negatively impact throughput of the mold.

Prior art molds for use in conjunction with the forming, molding and welding of tubing are in the nature of a composite or unitary assembly having the requisite parts associated with one another to form a unit. If a different mold is to be used to achieve a different operation of forming, molding and/or welding of the tubing, a new unit must be constructed. Without the capability of using substitutable subassemblies related to the mold itself, significant costs are incurred by having to develop a complete unit for each type of operation to be achieved.

IV tip manufacturing processes have been in operation a long time. Despite the maturity of the IV tip manufacturing process, there does not exist a reliable and consistent apparatus or methodology for capturing excess material resulting from the tip cutting process. In a typical IV tip manufacturing clean room, small particulates, byproducts of IV tip cuttings, cover the surroundings of an IV tipping station and demonstrates the lack of existing methodology to capture this debris.

Detecting the presence of tip debris can provide a signal to either an operator or a control circuit of the result of the tip cutting process. A lack of positive detection of the tip debris provides an alert to either the operator or the control circuit of a system failure. Such system failures may be indicative of production of bad parts. In an automated environment, a failure of this type may be a significant set back. Presently, detection of a system failure is a function of the lack of tip debris and reliance is placed solely upon an operator to continually remain observant.

SUMMARY OF THE INVENTION

Apparatus for forming, molding or welding thermoplastic tubing, includes a dissassembleable housing that supports various components and accommodates rapid and facile substitution of the components to satisfy the parameters of the various functions to be performed. A spool supporting a coil energized by radio frequency (RF) energy includes a central aperture surrounded by the coil and is supported by the housing. A mold having a center section extends through the aperture in the spool to locate the center section generally coincident with the coil. A manifold provides a flow of air into the space between the center section and the aperture to draw heat from the mold and to cool the mold after the tubing has been formed, molded or welded. The mold is removably mounted between the base and top of the housing to permit interchangeability. A passageway extending through the mold permits use of a mandrel to support the tubing for a tipping operation. The mandrel, in combination with the mold, causes severance of the tip of the tubing upon formation of a taper of the tubing. The housing supports a manifold that injects streams of air into the space between the aperture in the spool and to the center section of the mold coincident with the severed tip. Upon severance of the tip, the air streams urge translation of the severed tips through a passageway and into a collection chamber. Various sensors may be used to confirm severance of the tip and count the number of severed tips translated through the passageway.

It is therefore a primary object of the present invention to collect severed tips resulting from carrying out an IV tip manufacturing process.

Another object of the present invention is to provide a flow of air to cause translation of severed tips of molded tubing to a collection chamber.

Yet another object of the present invention is to provide a mandrel cooperating with a mold to sever the tip of a molded tubing.

Still another object of the present invention is to provide a collection chamber for severed tips of tubing.

A further object of the present invention is to provide a cooling airflow about a low mass mold and to urge translation of severed tips of IV tubing through a passageway and into a collection chamber.

A yet further object of the present invention is to provide a plurality of sensors to confirm severance of a tip and count the number of tips severed during a IV tubing tipping process.

A still further object of the present invention is to provide any of several differently configured mold subassemblies that may be interchangeably replaced within a housing to form, mold, or weld IV tubing and collect each tip severed from the tubing.

These and other objects of the present invention will become apparent to those skilled in the art as the description thereof proceeds.

BRIEF DESCRIPTION OF THE DRAWINGS

The present invention will be described with greater specificity and clarity with reference to the following drawings, in which:

FIGS. 4A, 4B, 4C and 4D illustrate various views of the mold assembly;

FIG. 5 illustrates an exploded view of the mold assembly;

DESCRIPTION OF THE PREFERRED EMBODIMENT

In the formation of IV tubing, sometimes referred to as a cannula tip or a stylet tip, the end of the tubing is tapered and the tip is cut off. The cut off tip amounts to debris to be discarded. In a production run, it is important to identify the presence of each cut off tip to ensure that the IV tubing is properly formed and that the manufacturing process is functioning normally. The apparatus for forming the IV tubing includes a source of air flow for cooling the attendant low mass mold. The air flow is also channeled through passageways to urge translation of the cut off tips past sensors for detecting the presence of cut off tips and into a collection chamber.

Figure 1:
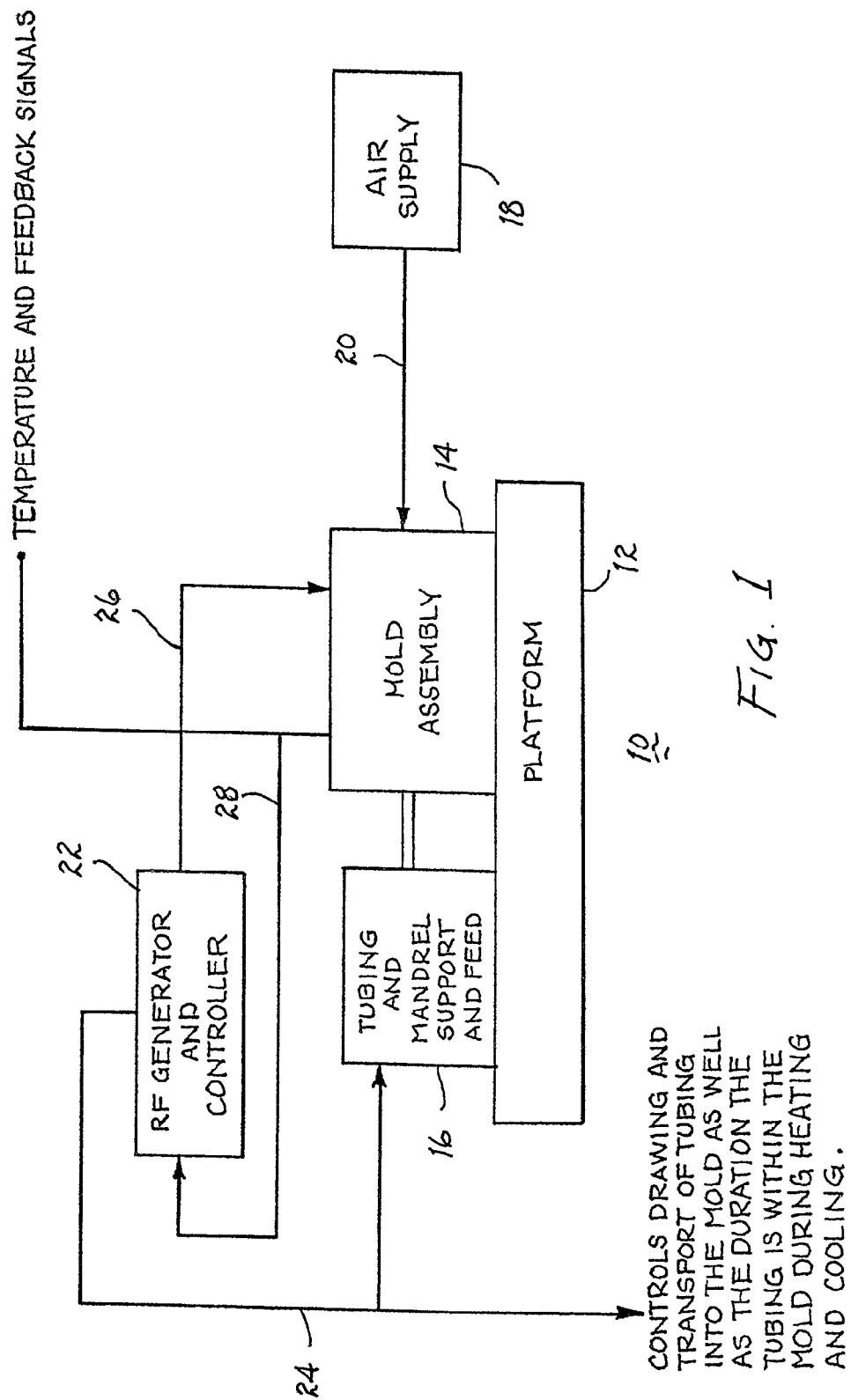
FIG. 1 is a schematic diagram illustrating major components of the present invention and their interconnections.

FIG. 1 illustrates a mold apparatus 10 for forming IV tubing. In particular, a platform or housing 12 supports mold assembly 14. The insertion and withdrawal of a mandrel, along with insertion and withdrawal of plastic tubing, into and from a mold assembly is provided by a support and feed unit 16. It is to be understood that this unit also supports the mandrel prior to and after insertion into the mold assembly. The air for mold cooling purposes is provided by air supply 18 conveying air under pressure through a conduit 20 to the mold assembly. An RF generator and control circuit is connected to support and feed unit 16 through conductor(s) 24. The signals transmitted by the control circuit through conductor(s) 24 may control the transport of the mandrel supported tubing into the mold, the duration the tubing is within the mold and the withdrawal of the tubing. Through a further conductor(s) 26, RF energy is supplied to a coil in a spool to cause the coil to inductively heat an encircled center section of a mold. A further conductor(s) 28 provides feedback signals to RF generator and control circuit 22. These feedback signals may be of many types, including temperature indication at one or more locations, signals reflective of the position of one or more of the moveable components and signals reflective of the air flow rate and/or temperature.

Figure 2:
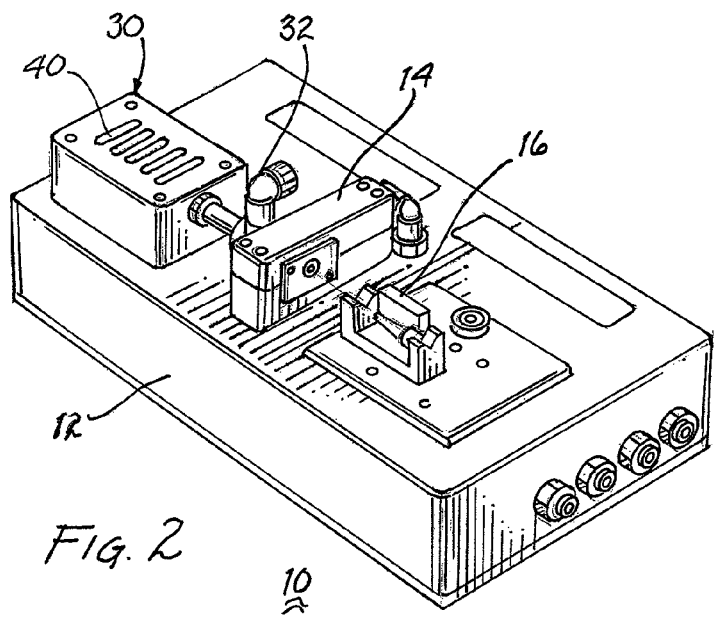
FIG. 2 illustrates the platform and the equipment mounted thereon.
Figure 3:
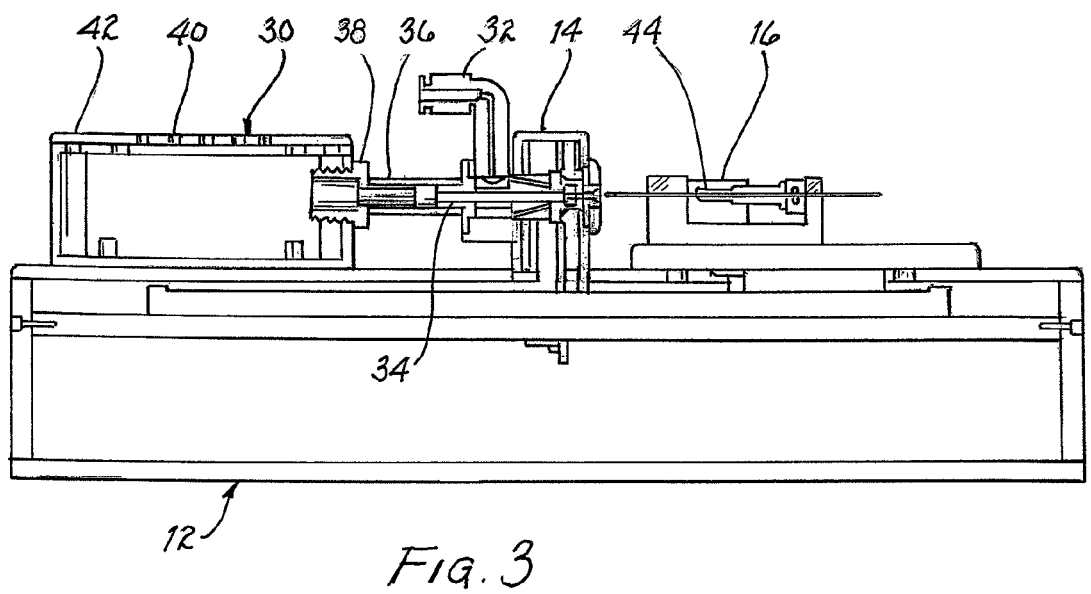
FIG. 3 is a cross sectional view of the platform and equipment illustrated in FIG. 2.

Referring jointly to FIGS. 2 and 3, there is illustrated an embodiment of mold apparatus 10. Housing 12 supports mold assembly 14, support and feed unit 16 and a collection chamber 30. The above described source of air supply 18 is connected to conduit 32 in fluid communication with the mold assembly. An air flow channel 34 extends from within mold assembly 14 into fluid communication with a pipe 36. This pipe is coupled with a hollow fitting 38 extending into collection chamber 30. The collection chamber includes a plurality of vents 40 that may be disposed in top 42 of the collection chamber. Unit 16 is slideably mounted on housing 12 to accommodate translation of mandrel supported IV tubing 44 into and out of mold assembly 14.

Referring jointly to FIGS. 4A, 4B, 4C and 4D there is shown mold assembly 14 having enclosure 50 formed by a bottom 52 and a top 54. A manifold 56 is disposed on the left side and is in fluid communication with a conduit 32 functionally connected to a source of air under pressure (not shown). A flange 58 of a mold 60 may extend from the right side of enclosure 50, as illustrated. A pair of conductors 62 may extend from within the enclosure for connection to an RF generator.

Referring particularly to FIGS. 4B, 4C, and 4D, certain structure internal to enclosure 50 will be described. Top 54 and bottom 52 of enclosure 50 are secured to one another by bolts 64, 66 extending through apertures in top 54 and into threaded engagement with bottom 52. Mold 60 extends into enclosure 50 and may be threadedly engaged with cone 68 disposed within manifold 56. A spool 70 includes a central aperture for penetrable engagement with mold 60. Conductors 62 are wrapped about the spool to form a coil and, upon energization, will cause inductive heating of the circumscribed central section of the mold.

FIG. 5 illustrates an exploded view of the basic components supported by enclosure 50. Manifold 56 includes a cylinder 72 having a cone shaped interior surface commensurate with the surface of cone 68 but of larger size to provide a cone shaped space therebetween. Cylinder 72 includes an inlet 74 in fluid communication with conduit 32 to introduce air into the space between the cylinder and the cone. Cylinder 72 includes an annular ridge 76 for engagement with a correspondingly sized partial annular groove 78 formed in bottom 52 and a partial annular groove 80 formed in top 54. Spool 70 includes a threaded passageway 84 in at least one of the discs forming the spool and a further passageway 86 in each of the discs forming the spool. A machine screw 88 is supported intermediate bottom 52 and top 54 in commensurately configured grooves and it is in threaded engagement with threaded passageway 84. A pin 90 is rotatably supported in commensurate grooves in bottom 52 and top 54 and is in non threaded penetrable engagement with passageways 86. Upon rotation of screw 88, spool 70 will be translated left to right and right to left and rotation of the spool is precluded by its sliding engagement with pin 90. Mold 60 extends through and in non contacting relationship with aperture 92 formed at the center of spool 70 to form an annular space between the aperture and the encircled mold. In one embodiment, end 94 of the mold may be in threaded engagement with the center of cone 68.

Figure 6:
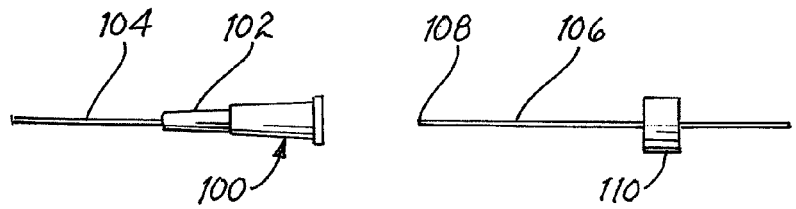
FIG. 6 illustrates a cannula tip and a mandrel for insertion therein.
Figure 7:
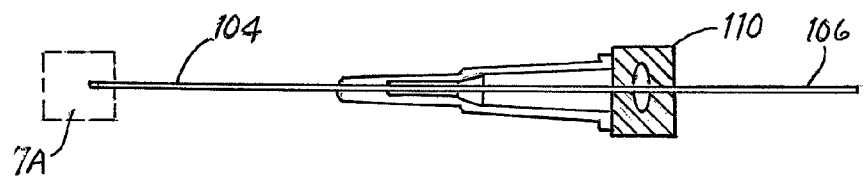
FIG. 7 illustrates the mandrel inserted within the cannula tip.

Referring to FIG. 6, there is shown IV tubing 100 formed by a body 102 supporting a length of plastic tubing 104 extending therefrom and prior to formation of a taper at the tip of the tubing. A mandrel 106 includes an end 108 having an annular sharp edge. A collet 110 is mounted on the mandrel at a location commensurate with a predetermined penetration of the mandrel through tubing 104. Referring jointly to cross sectional views in FIGS. 7 and 7A, mandrel 106 is shown inserted through body 102 and into tubing 104. The degree of insertion of the mandrel within the tubing is a function of the degree of extension 112 of the tubing past end 108 of the mandrel. For different diametric sizes and wall thicknesses of the tubing, the length of extension 112 may vary. It may be noted that the degree of extension of the mandrel within the tubing is a function of the location of collet 110 upon the mandrel; this location is adjustable as a function of the characteristics of the tubing and the nature of the tipping to be performed on the IV tubing.

Figure 8:
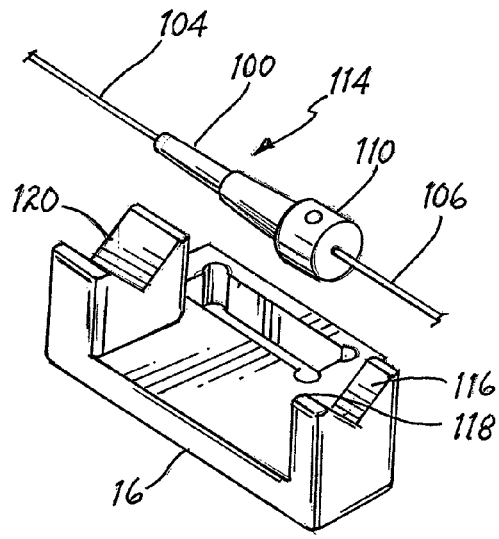
FIG. 8 illustrates the support and feed unit for receiving the cannula tip and mandrel.

Referring to FIG. 8, there is illustrated support and feed unit 16 prior to placing assembly 114, consisting of IV tubing 100, mandrel 106 and collet 110, thereon. The support and feed unit includes a V-shaped support 116 for supporting mandrel 106 at the apex of the support. The interior side 118 of unit 16 bears against the rear surface of collet 110. A further V-shaped support 120 supports a combination of tubing 104 and internally located mandrel 106. By using V-shaped supports of this type, the mounting of assembly 114 is an easily accomplished task. By using the V-shaped supports, self-alignment of assembly 114 with support and feed unit 16 is automatic. Furthermore, after the tip of the tubing has been formed, removal of assembly 114 amounts to nothing more than lifting the assembly from the feed and support unit.

Figure 9:
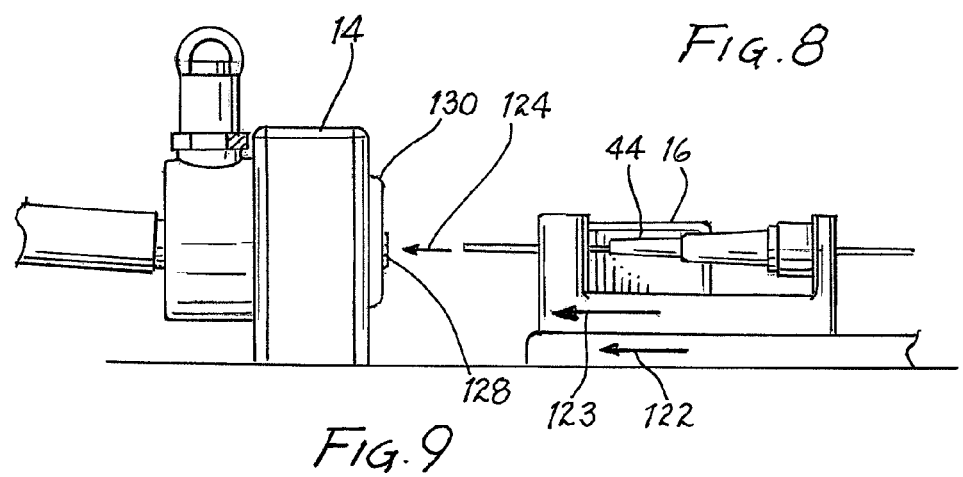
FIG. 9 illustrates the translation of the support and feed unit toward the mold assembly.
Figure 9A:
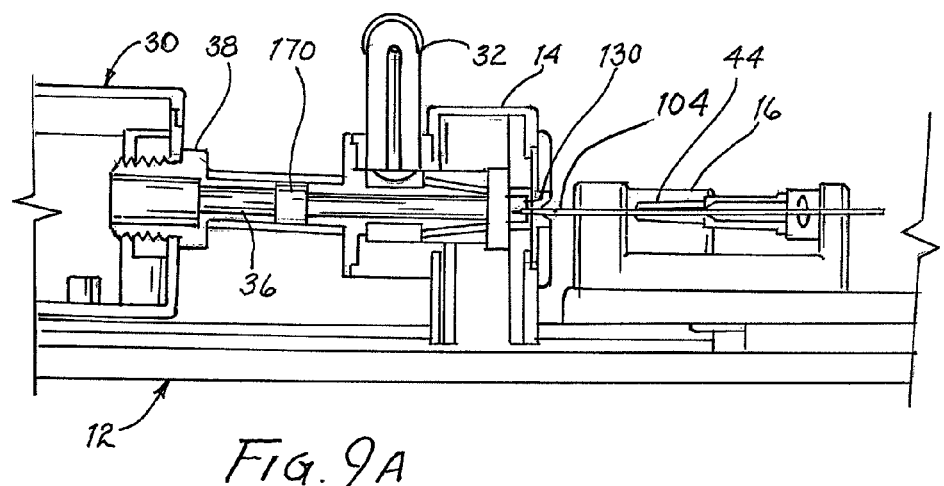
FIG. 9A is a cross sectional view illustrating the IV tubing and mandrel inserted within a mold.

After mounting assembly 114 on support and feed unit 16, the unit is translated toward mold assembly 14 as depicted by arrows 122, 123 and 124 in FIG. 9. Supports 116, 120 of the support and feed unit accurately align tubing 104 and supporting mandrel 106 with inlet 128 of mold 130. This mold is equivalent to mold 60 illustrated in FIGS. 4A, 4C, 4B and 5. On completion of translation of the support and feed unit, as depicted in the cross sectional view shown in FIG. 9A, mandrel supported tubing 104 is lodged within mold 130.

Figure 7A:
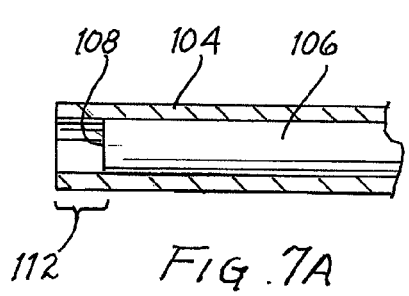
FIG. 7A is a partial view taken within the dashed lines shown in FIG. 7.
Figure 10:
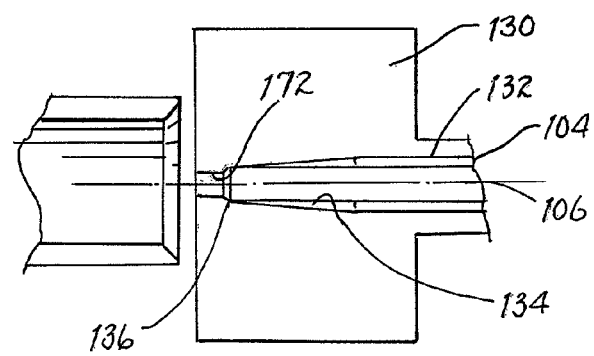
FIG. 10 is a detailed view illustrating the interaction of the mandrel with the mold.
Figure 11:
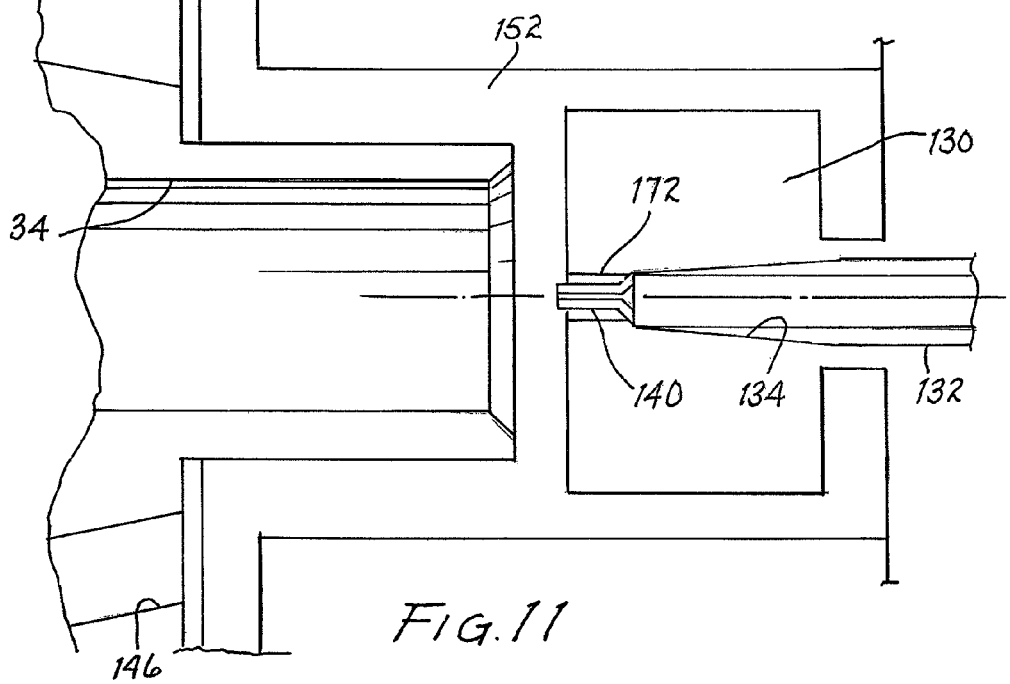
FIG. 11 illustrates the severed tip of the IV tubing.

Upon insertion of mandrel 106 supported tubing 104 (assembly 114), mold 130 is heated. As particularly depicted in FIGS. 10 and 11, the mold includes a cylindrical section 132 terminating in a shallow cone shaped section 134. The end of section 134 includes a truncated cone shaped section 136 having a more angular orientation relative to cone shaped section 134 and an internal diameter less than the diameter of mandrel 106. Upon extension of mandrel 106 into mold 130, end 108 (see FIG. 7A) will bear against and come into contact with truncated cone shaped section 136. Because of the sharp circumferential edge of end 108, it will cause a cutting of extension 112 of tubing 104 extending beyond the end of the mandrel, as shown in FIG. 7A. This cutting function produces a severed tip 140 lying within circular passageway 142 of mold 130.

Figure 12:
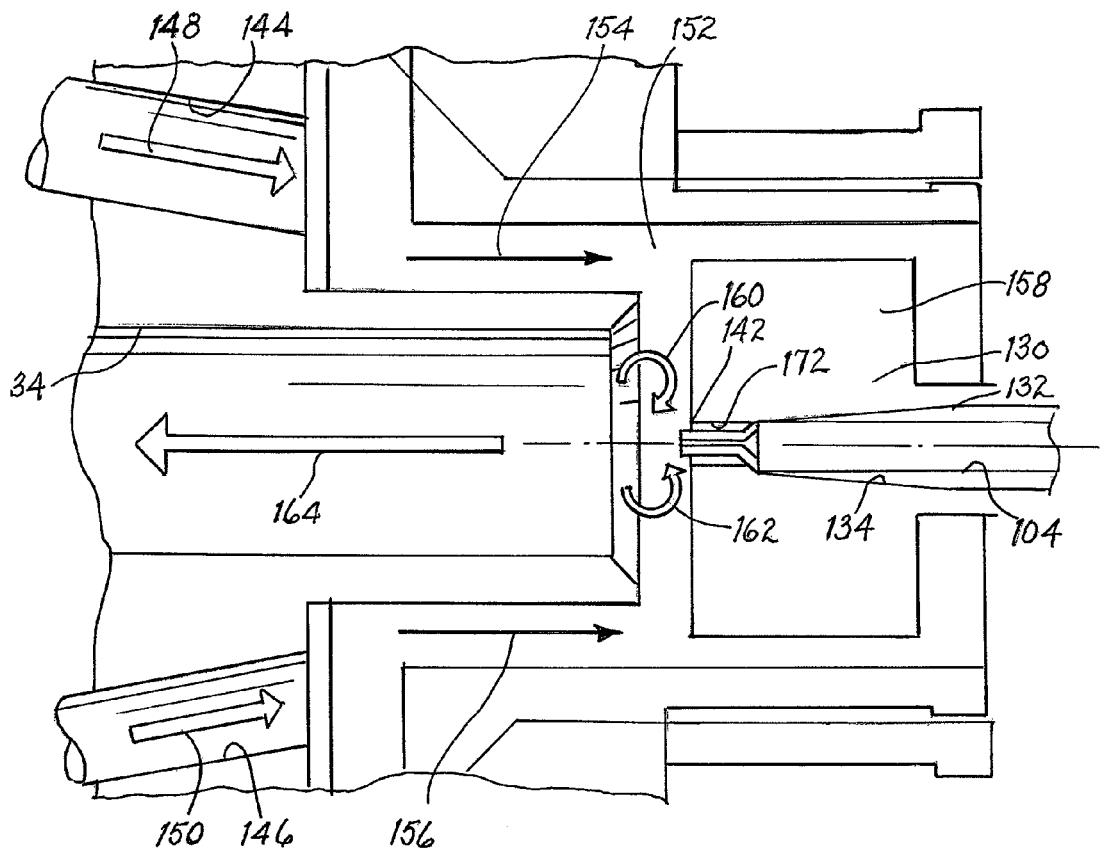
FIG. 12 illustrates the turbulent air attended the severed tip of the IV tubing.
Figure 13:
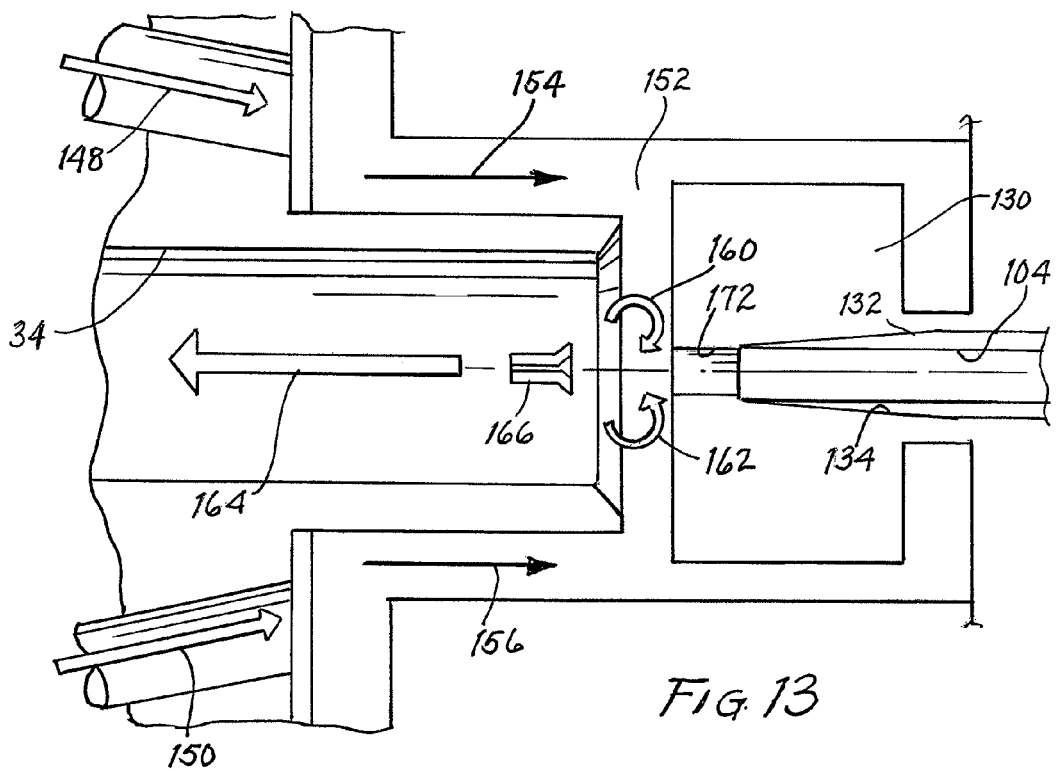
FIG. 13 illustrates the translation of the severed tip through a passageway to a collection chamber.

As depicted in FIG. 3 and FIG. 12, conduit 32 is in fluid communication with a source of air flow for cooling mold assembly 14. This air flow is channeled through passageways 144, 146, as depicted by arrows 148, 150. The air flow continues from each of these passageways to a common chamber 152, as depicted by arrows 154 and 156. This chamber surrounds section 158 of mold 130 wherein tubing 104 is actually formed into a tapered configuration. As depicted by circular arrows 160, 162 proximate opening 172 of passageway 142, turbulent air flow will exist adjacent to the opening and into passageway 142. This turbulent air flow is exhausted through channel 34 (see also FIG. 3), as depicted by arrow 164. The turbulent air flow (arrows 160, 162 depicted in FIGS. 12, 13, 14 and 15) will have the effect of extracting severed tip 166 from within passageway 142. Furthermore, the air flow (depicted by arrows 164 through channel 34) will urge translation of severed tip 166 along the channel as illustrated in FIG. 13.

Figure 14:
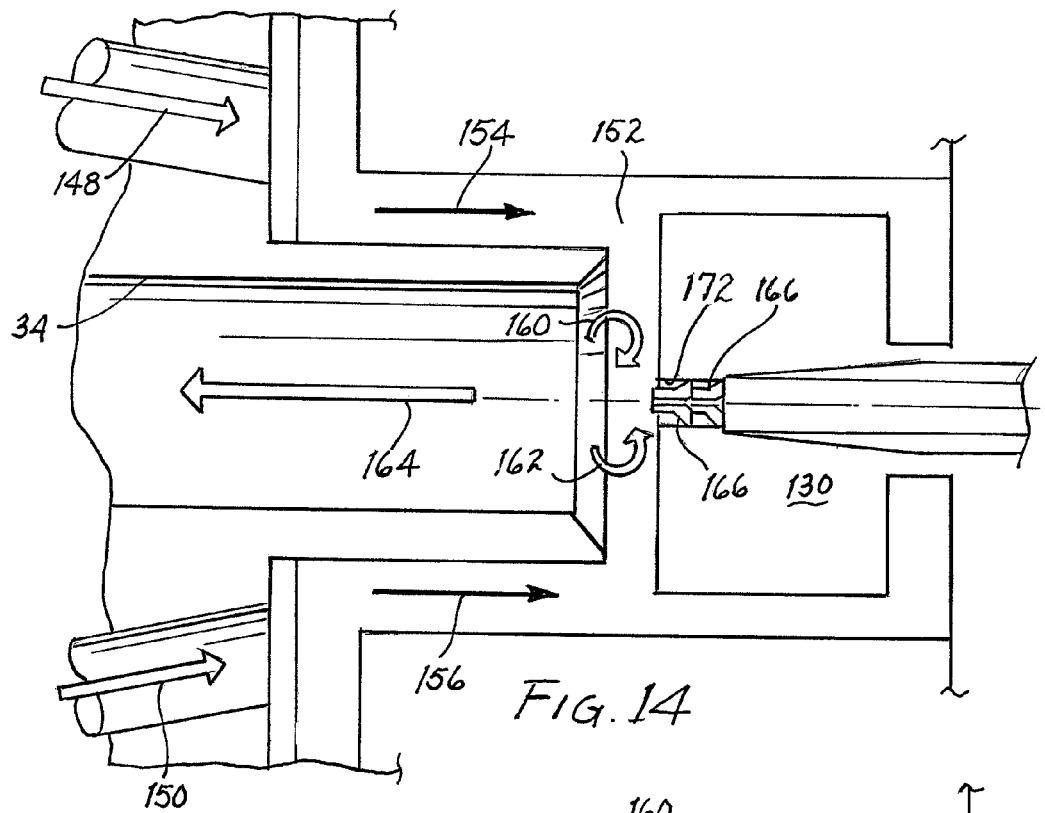
FIG. 14 illustrates a potential plurality of severed tips.
Figure 15:
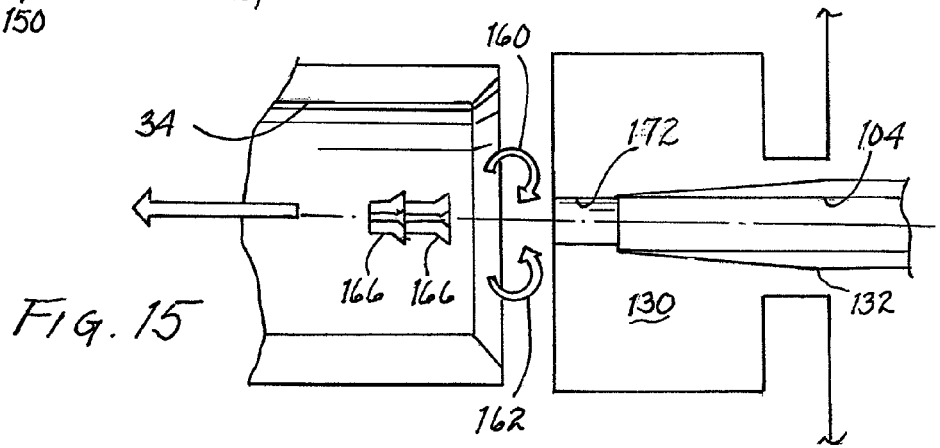
FIG. 15 illustrates the translation of a plurality of tips through a passageway in response to an imposed air flow.

Under certain circumstance a severed tip 166 may remain lodged within passageway 142 instead of being extracted by the adjacent turbulent air flow. Such situation is depicted in FIG. 14 wherein two severed tips are lodged within the passageway. Subsequent molding operations will produce an additional severed tip with each operation. The accumulation of these severed tips will result in the front most tip ultimately becoming directly subjected to the turbulent air flow attendant opening 172 of passageway 142. Because the severed tips are relatively light weight and the turbulent air flow exerts a force thereon, extraction of a foremost tip will ultimately occur. With the extraction of the foremost severed tip, a greater or lesser extraction force due to turbulent air flow within passageway 142 will urge extraction of any remaining severed tips. Upon such extraction, one or more severed tips will be conveyed into channel 34 as depicted in FIG. 15.

Figure 16:
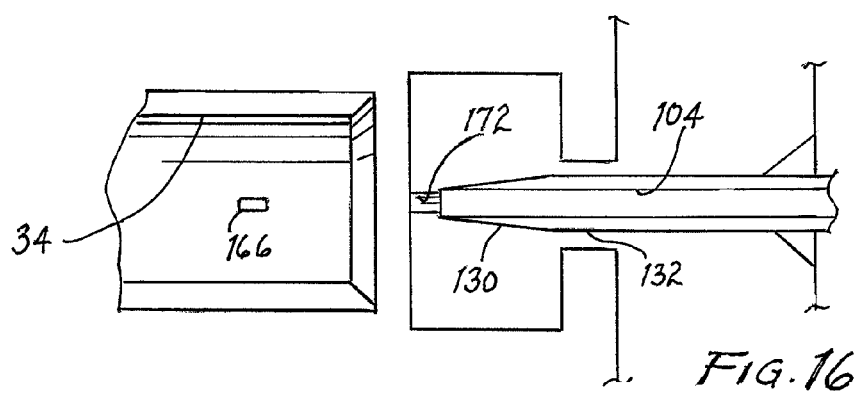
FIG. 16 illustrates translation of a severed tip through a passageway.
Figure 17:
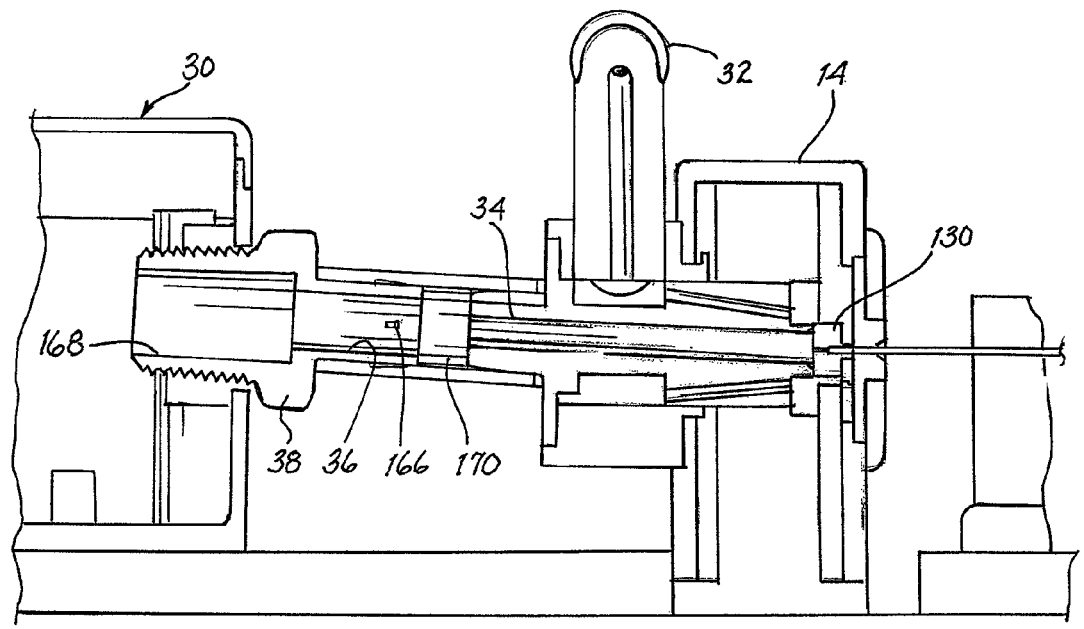
FIG. 17 illustrates further translation of the severed tip.
Figure 18:
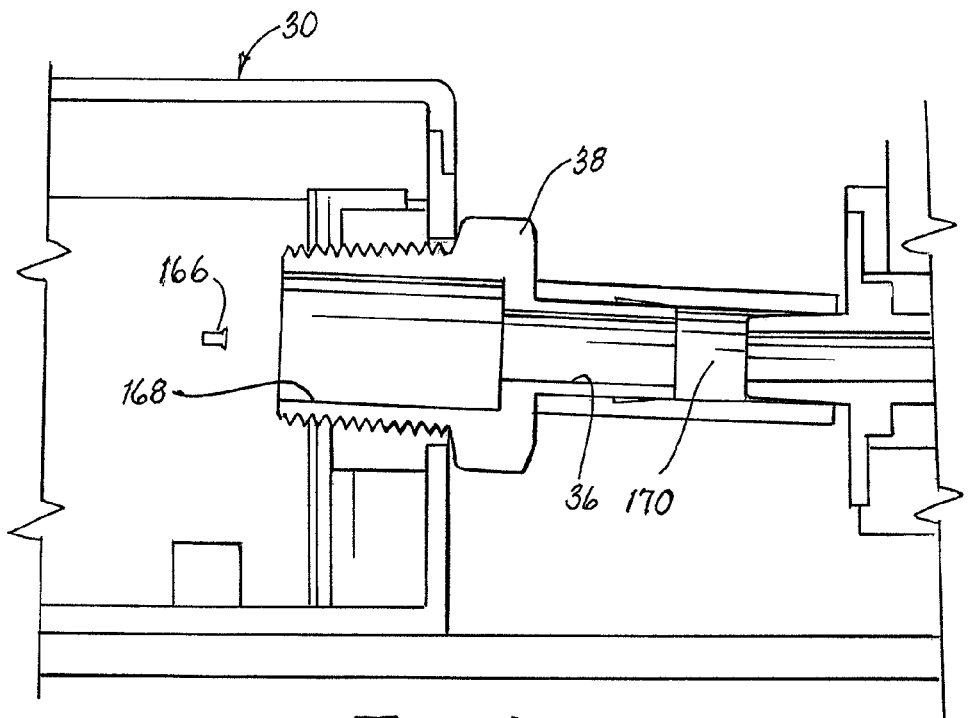
FIG. 18 illustrates the severed tip arriving within a collection chamber.

As depicted in FIGS. 16, 17 and 18, severed tip 166 will be translated through channel 34 into pipe 36. Thereafter it will flow into fitting 38 and be exhausted therefrom into collection chamber 30. As depicted in the drawings, the diameter of channel 34 is less than the diameter of pipe 36. Such increase in diameter will result in proportional decrease of flow rate of the air flowing therethrough. Fitting 38 includes a cylindrical passageway 168 of a diameter significantly greater than that of pipe 36. The commensurate reduction in air flow rate will slow the translation of severed tip 166 therethrough. With the reduced translation speed of the severed tip, it is likely that it will drop to the bottom of collection chamber 30. Moreover, the reduced air flow rate exhausting from passageway 168 will have a minimal effect upon any movement of severed tips already lodged in the collection chamber. As noted with respect to FIG. 3, the collection chamber includes vents 40 in the top surface for exhausting the air flow. The combined area of the these exhaust vents is significantly greater than the cross sectional area of passage 168 which causes the rate of flow of exhaust air to be significantly reduced. Such reduction in flow rate minimizes the likelihood of any severed tips becoming lodged in the exhaust vents.

As represented by module 170 disposed intermediate channel 34 and pipe 36, shown in FIG. 17, sensors of any of various types may be lodged therein or elsewhere along the length of channel 34, pipe 36 or passageway 168 to sense translation of a severed tip there passed. In a high production or mass production version of the present invention it may become critical to ensure the passage of each severed tip commensurate with the formation of the IV tubing. Without such confirmation, there may be an indication of faulty operation, breakage, or other production halting situation. To minimize downtime and to ensure accuracy and completeness of the IV tubing formation process, such sensing may be critical.

I claim:

1. Apparatus for forming IV tubing, said apparatus comprising in combination:
   a) a low mass mold assembly including a mold cavity for forming the IV tubing with a tapered end;
   b) a mandrel inserted within the IV tubing for a distance less than the length of the IV tubing to define an extension of the IV tubing;
   c) said mold cavity including a truncated cone section for interferingly engaging the end of said mandrel to sever the tip of the IV tubing corresponding with the extension;
   d) a passageway extending from adjacent to said mold cavity for translating the tip from said mold cavity;
   e) a collection chamber disposed at the termination of said passageway; and
   f) a source of air flow for urging translation of the tip from said mold cavity through said passageway and into said collection chamber.

2. The apparatus as set forth in claim 1 including a support and feed unit for transporting the mandrel supported IV tubing into and out of engagement with said mold cavity.

3. The apparatus as set forth in claim 2 wherein said IV tubing includes a length of tubing and a body supporting the tubing and wherein the mandrel extends from the body and including a collet mounted on the mandrel bearing against the body to limit the degree of insertion of the mandrel into the tubing.

4. The apparatus as set forth in claim 3 wherein said support and feed unit includes a first V shaped support for supporting the tubing with inserted mandrel and a second V shaped support for supporting the mandrel and in contact with said collet.

5. The apparatus as set forth in claim 1 wherein the cross sectioned area of said passageway increases from said mold cavity to said collection chamber to reduce the rate of air flow and the rate of translation of the severed tip through said passageway.

6. The apparatus as set forth in claim 1 wherein said mold cavity includes a passageway for receiving the severed tip and subject to the air flow to urge extraction of the severed tip and translation into said passageway extending from adjacent to said mold cavity.

7. The apparatus as set forth in claim 1 including at least one sensor for sensing translation of a severed tip through said passageway.

8. The apparatus as set forth in claim 1 wherein said collection chamber includes a top and a plurality of vents disposed in said top.

9. The apparatus as set forth in claim 8 wherein the combined cross sectional area of said plurality of vents is greater than the cross sectional area of said passageway to reduce the rate of flow of air through said plurality of vents.

10. Apparatus for collecting severed tips of IV tubing extending from a taper to the end IV tubing formed in a mold cavity, said apparatus comprising in combination:
    a) a mandrel inserted within the IV tubing and terminating short of the end of the IV tubing to define an extension of the IV tubing and the tip;
    b) a sharp annular edge formed at the end of said mandrel for interfering engagement with a truncated cone of the mold cavity to sever the tip from the IV tubing;
    c) a passageway;
    d) a source of air flow for urging translation of the tip from within the mold cavity into said passageway; and
    e) a collection chamber, wherein the severed tip is conveyed through said passageway into said collection chamber in response to the air flow through said passageway.

11. The apparatus as set forth in claim 10 including a support and feed unit for inserting said mandrel supported IV tubing into the mold cavity and for withdrawing said mandrel supported IV tubing from the mold cavity.

12. The apparatus as set forth in claim 11 including a collet attached to said mandrel extending from the IV tubing for limiting the degree of insertion of said mandrel into the IV tubing.

13. The apparatus as set forth in claim 10 wherein the cross sectional area of said passageway is increased between the mold cavity and said collection chamber to reduce the rate of flow of the air flow therethrough.

14. The apparatus as set forth in claim 13 wherein said collection chamber includes a plurality of exhaust vents and wherein the total cross sectional area of said exhaust vents is greater than the cross sectional area of said passageway.

15. The apparatus as set forth in claim 10 including at least one sensor for sensing translation of a tip through said passageway.

* * * * *